United States Patent
Viscomi et al.

(10) Patent No.: US 8,853,231 B2
(45) Date of Patent: *Oct. 7, 2014

(54) PHARMACEUTICAL COMPOSITIONS COMPRISING POLYMORPHIC FORMS α, β, AND γ OF RIFAXIMIN

(71) Applicant: Alfa Wassermann, S.p.A., Bologna (IT)

(72) Inventors: Giuseppe Claudio Viscomi, Bologna (IT); Manuela Campana, Bologna (IT); Dario Braga, Bologna (IT); Donatella Confortini, Bologna (IT); Vincenzo Cannata, Bologna (IT); Paolo Righi, Bologna (IT); Goffredo Rosini, Bologna (IT)

(73) Assignee: Alfa Wassermann S.p.A., Alanno (PE) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/679,602

(22) Filed: Nov. 16, 2012

(65) Prior Publication Data

US 2013/0289269 A1 Oct. 31, 2013

Related U.S. Application Data

(63) Continuation of application No. 13/448,347, filed on Apr. 16, 2012, now abandoned, which is a continuation of application No. 13/041,347, filed on Mar. 4, 2011, now Pat. No. 8,158,644, which is a continuation of application No. 12/119,622, filed on May 13, 2008, now Pat. No. 7,906,542, which is a continuation-in-part of application No. 11/873,841, filed on Oct. 17, 2007, now Pat. No. 7,915,275, which is a continuation-in-part of application No. 11/135,651, filed on May 24, 2005, now abandoned, which is a continuation-in-part of application No. PCT/EP2004/012490, filed on Nov. 4, 2004.

(30) Foreign Application Priority Data

Nov. 7, 2003 (IT) .............................. MI03A002144

(51) Int. Cl.
*A61K 31/395* (2006.01)
*C07D 498/22* (2006.01)
*A61K 31/437* (2006.01)

(52) U.S. Cl.
CPC ............ *C07D 498/22* (2013.01); *A61K 31/437* (2013.01)
USPC ........................................................ 514/279

(58) Field of Classification Search
USPC ........................................................ 514/279
See application file for complete search history.

*Primary Examiner* — Bruck Kifle
(74) *Attorney, Agent, or Firm* — Steinfl & Bruno LLP

(57) ABSTRACT

Crystalline polymorphous forms of rifaximin (INN), referred to as rifaximin α and rifaximin β, and a poorly crystalline form referred to as rifaximin γ, useful in the production of medicaments containing rifaximin for oral and topical use and obtained by means of a crystallization process carried out by hot-dissolving the raw rifaximin in ethyl alcohol and by causing the crystallization of the product by addition of water at a fixed temperature and for a fixed period of time, followed by a drying under controlled conditions until reaching a precise water content in the end product, are the object of the invention.

18 Claims, 3 Drawing Sheets

PHARMACEUTICAL COMPOSITIONS COMPRISING POLYMORPHIC FORMS α, β, AND γ OF RIFAXIMIN

APPLICATION PRIORITY DATA

This application is a continuation of U.S. application Ser. No. 13/041,347, filed Mar. 4, 2011, now U.S. Pat. No. 8,158,644, issued on Apr. 17, 2012, which in turn is a continuation of U.S. application Ser. No. 12/119,622, filed May 13, 2008, now U.S. Pat. No. 7,906,542, issued on Mar. 15, 2011, which in turn is a continuation-in-part of application U.S. application Ser. No. 11/873,841, filed on Oct. 17, 2007, now U.S. Pat. No. 7,915,275, issued on Mar. 29, 2011, which is a continuation-in part of U.S. application Ser. No. 11/135,651, filed on May 24, 2005, now abandoned, which is a continuation-in-part of PCT/EP04/12490, filed on Nov. 4, 2004, which claims priority to Italian application No. MI2003A002144 filed Nov. 7, 2003, all of which are incorporated by reference herein in their entirety, including any drawings.

BACKGROUND OF THE INVENTION

1. Field of the Invention

The present invention relates to rifaximin polymorphic forms α, β and γ, the processes for their preparation and the use thereof in the manufacture of medicinal preparations.

2. Description of the Related Art

Rifaximin (INN; see The Merck Index, XIII Ed., 8304) is an antibiotic belonging to the rifamycin class, namely a pyrido-imidazo rifamycin described and claimed in Italian Patent IT 1154655, while EP 0161534 discloses and claims a process for its production starting from rifamycin O (The Merck Index, XIII Ed., 8301).

Both these patents generically describe the purification of rifaximin by crystallization in suitable solvents or solvent systems and summarily show in some examples that the resulting product can be crystallized from the 7:3 mixture of ethyl alcohol/water and dried both under atmospheric pressure and under vacuum. Neither information concerning the experimental conditions of crystallization and drying, nor any distinctive crystallographic characteristic of the obtained product are reported.

The presence of different polymorphs had not been ascertained and therefore the experimental conditions described in both patents had been developed with the aim of obtaining a homogeneous product having suitable purity from the chemical point of view, apart from the crystallographic aspects of the product itself.

It has now been unexpectedly found that some polymorphic forms of rifaximin exist whose formation depends on the solvent as well as on the conditions of time and temperature at which both crystallization and drying are carried out.

SUMMARY OF THE INVENTION

In one embodiment, a pharmaceutical composition is provided comprising rifaximin in polymorphic form α. In one embodiment, the $C_{max}$ is about 2 ng/ml. In a further embodiment, the $C_{max}$ is about 2.6 ng/ml. In one embodiment, the $t_{max}$ is about 9 hours. In a further embodiment, the $t_{max}$ is about 9.5 hours. In other embodiments, the $AUC_{0-24\,h}$ is about 13 ng·h/ml.

In another embodiment, the pharmaceutical composition provided comprising rifaximin in polymorphic form α has a water content of from between about 0% to about 3%. In one embodiment, the $C_{max}$ is about 2 ng/ml. In a further embodiment, the $C_{max}$ is about 2.6 ng/ml. In one embodiment, the $t_{max}$ is about 9 hours. In a further embodiment, the $t_{max}$ is about 9.5 hours. In other embodiments, the $AUC_{0-24\,h}$ is about 13 ng·h/ml.

In other embodiments, a pharmaceutical composition is provided comprising rifaximin in polymorphic form β. In one embodiment, the $C_{max}$ is about 1 ng/ml. In a further embodiment, the $C_{max}$ is about 1.1 ng/ml. In one embodiment, the $t_{max}$ is about 4 hours. In a further embodiment, the $t_{max}$ is about 9.5 hours. In other embodiments, the $AUC_{0-24\,h}$ is about 11 ng·h/ml. In one embodiment, the intrinsic dissolution rate of the rifaximin is about 0.01 mg/min/cm$^2$.

In another embodiment, the pharmaceutical composition provided comprising rifaximin in polymorphic form β has a water content of from between greater than about 4.5%. In one embodiment, the $C_{max}$ is about 1 ng/ml. In a further embodiment, the $C_{max}$ is about 11 ng/ml. In one embodiment, the $t_{max}$ is about 4 hours. In a further embodiment, the $t_{max}$ is about 9.5 hours. In other embodiments, the $AUC_{0-24\,h}$ is about 11 ng·h/ml. In one embodiment, the intrinsic dissolution rate is about 0.01 mg/min/cm$^2$.

In other embodiments, a pharmaceutical composition is provided comprising rifaximin in polymorphic form γ. In one embodiment, the $C_{max}$ is about 670 ng/ml. In a further embodiment, the $C_{max}$ is about 668 ng/ml. In one embodiment, the $t_{max}$ is about 2 hours. In a further embodiment, the $t_{max}$ is about 2.3 hours. In other embodiments, the $AUC_{0-24\,h}$ is about 4000 ng·h/ml.

In another embodiment, the pharmaceutical composition provided comprising rifaximin in polymorphic form γ has a water content of from between about 1% to about 2%. In one embodiment, the $C_{max}$ is about 670 ng/ml. In a further embodiment, the $C_{max}$ is about 668 ng/ml. In one embodiment, the $t_{max}$ is about 2 hours. In a further embodiment, the $t_{max}$ is about 2.3 hours. In other embodiments, the $AUC_{0-24\,h}$ is about 4000 ng·h/ml.

Another embodiment of the invention provides a pharmaceutical composition comprising one or more of a form α, a form β, and a form γ polymorph of rifaximin and a pharmaceutically acceptable carrier. In one embodiment, the pharmaceutical composition further comprises excipients. In a further embodiment, the excipients are one or more of a diluting agent, binding agent, lubricating agent, disintegrating agent, colouring agent, flavouring agent or sweetening agent.

In one embodiment, the composition is formulated for selected coated and uncoated tablets, hard and soft gelatine capsules, sugar-coated pills, lozenges, wafer sheets, pellets and powders in a sealed packet.

One embodiment of the invention provides a pharmaceutical composition consisting essentially of rifaximin in polymorphic form α.

Another embodiment of the invention provides a pharmaceutical composition consisting essentially of rifaximin in polymorphic form β.

A further embodiment of the invention provides a pharmaceutical composition consisting essentially of rifaximin in polymorphic form γ.

DETAILED DESCRIPTION OF THE PREFERRED EMBODIMENT

Figure 1:
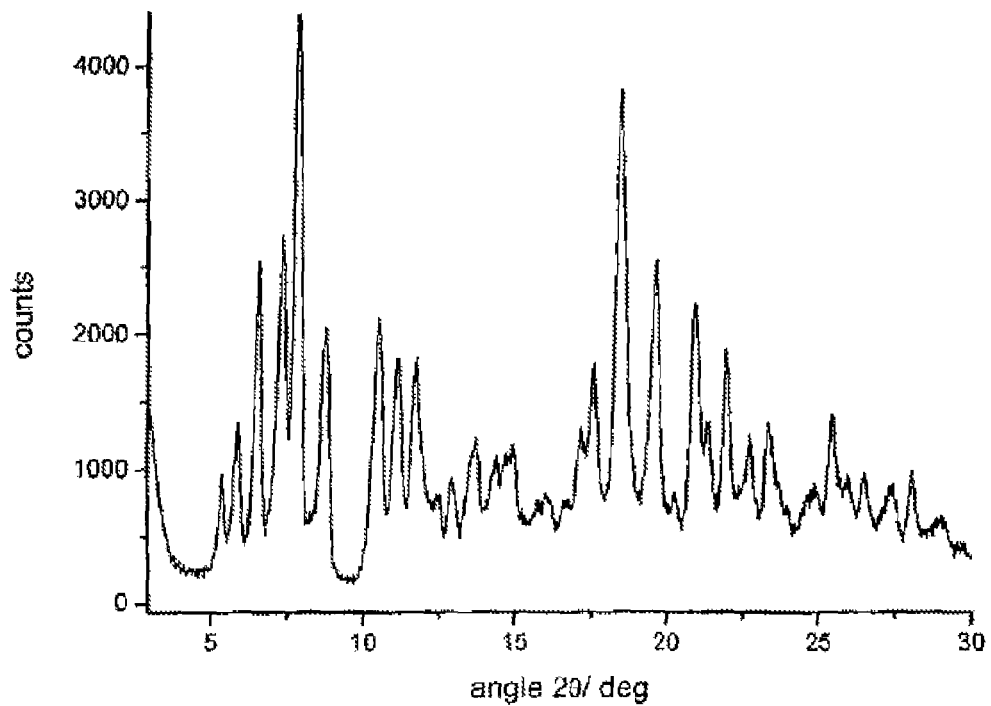
FIG. 1 is a powder X-ray diffractogram of rifaximin polymorphic form α.

The present invention relates to the form α, the form β and the form γ of the antibiotic known as rifaximin (INN), the processes for their preparation and the use thereof in the manufacture of medicinal preparations for the oral or topical route.

The process of the present invention comprises reacting one molar equivalent of rifamycin O with an excess of 2-amino-4-methylpyridine, preferably from 2.0 to 3.5 molar equivalents, in a solvent mixture consisting of water and ethyl alcohol in volumetric ratios between 1:1 and 2:1, for a time between 2 and 8 hours at a temperature between 40° C. and 60° C.

After completion of the reaction, the reaction mass is cooled to room temperature and added with a solution of ascorbic acid in a mixture of water, ethyl alcohol and aqueous concentrated hydrochloric acid, under strong stifling, in order to reduce the small amount of oxidized rifaximin that forms during the reaction. Finally the pH is adjusted to about 2.0 by further addition of hydrochloric acid concentrated aqueous solution, in order to better remove the excess of 2-amino-4-methylpyridine used in the reaction. The suspension is filtered and the resulting solid is washed with the same solvent mixture water/ethyl alcohol as used in the reaction. Such semifinished product is called "raw rifaximin".

The raw rifaximin can be directly submitted to the subsequent purification step. Alternately, in case long times of preservation of the semifinished product are expected, the raw rifaximin can be dried under vacuum at a temperature lower than 65° C. for a time between 6 and 24 hours, such semifinished product is called "dried raw rifaximin".

The resulting raw rifaximin and/or dried raw rifaximin are purified by dissolution in ethyl alcohol at a temperature between 45° C. and 65° C., followed by crystallization by addition of water, preferably in weight amounts between 15% and 70% to the weight amount of ethyl alcohol used for the dissolution, and by keeping the resulting suspension at a temperature between 50° C. and 0° C. under stirring during a time between 4 and 36 hours.

The suspension is filtered and the obtained solid is washed with water and dried under vacuum or under normal pressure, optionally in the presence of a drying agent, at a temperature between room temperature and 105° C. for a time between 2 and 72 hours.

The achievement of the α, β and γ forms depends on the conditions selected for the crystallization. In particular, the composition of the solvent mixture used for the crystallization, the temperature at which the reaction mixture is kept after the crystallization and the period of time at which that temperature is kept, have proven to be critical.

More precisely, rifaximin γ is obtained when the solution is brought to a temperature between 28° C. and 32° C. to start precipitation and the resulting suspension is further cooled to 0° C. and kept at this temperature for a time between 6 and 24 hours.

The suspension is filtered, the solid is washed with demineralized water and is dried to a water content between 1.0% and 2.0%.

The α and β rifaximins are obtained when the temperature is first brought to a value between 28° C. and 32° C. in order to start crystallization, then the suspension is brought to a temperature between 40° C. and 50° C. and kept at this value for a time between 6 and 24 hours, then the suspension is quickly cooled to 0° C. in 15 minutes to one hour, then is filtered, the solid is washed with water and then dried.

The drying steps plays an important role in obtaining the rifaximin α and β polymorphic forms and has to be monitored by a method suited to water dosage, such as the Karl Fischer method, in order to check the amount of remaining water present in the product under drying.

Rifaximin α or rifaximin β are obtained by drying to different final water contents, be they higher or lower than 4.5%, and do not depend on the experimental conditions of pressure and temperature at which such critical water contents are achieved. In fact, the two polymorphic forms, with higher or lower water content, can be obtained by drying under vacuum or at atmospheric pressure, at room temperature or at high temperatures, optionally in the presence of drying agents, provided that the drying is prolonged for the time necessary to reach the water content characteristic for each polymorphic form.

The polymorphic form β is obtained when the drying of the product crystallized and washed with water is stopped at water contents higher than 4.5%, measured by Karl Fischer, preferably between 5.0% and 6.0%, while the polymorphic form α is obtained when drying is continued until water contents lower than 4.5%, preferably between 2.0% and 3.0%.

Both the form γ and the forms α and β of rifaximin are hygroscopic, they reversibly absorb water in time in the presence of suitable environmental conditions of pressure and humidity and are susceptible of transformation from one form into another.

When the polymorphic form α is kept under conditions of relative humidity higher than 50% for a time between 12 and 48 hours, it changes into the polymorphic form β, which in its turn is transformed into the polymorphic form α upon drying to a water content lower than 4.5%, preferably comprised between 2.0% and 3.0%.

Another type of transition exists between the form γ and the forms α and β, depending upon the temperatures kept during the phase of precipitation of rifaximin.

In particular, the form γ turns into the forms α or β when a suspension of the form γ of rifaximin is kept in an ethyl alcohol/water 7:3 (V/V) solvent mixture at a temperature between 38° C. and 50° C. under strong stifling for a prolonged time, preferably comprised between 6 and 36 hours.

After filtration and washing with demineralized water, drying to a water content higher than 4.5%, preferably between 5.0% and 6.0%, affords the polymorphic form β, while when drying is continued to a water content lower than 4.5%, preferably between 2.0% and 3.0%, gives the form α.

Rifaximins α and β can in their turn change into rifaximin γ by dissolution in ethyl alcohol and treatment of the resulting solution as previously described for the preparation of the form γ.

These transitions from one form into another are very important for the invention, as they can be provide an alternative process for the preparation of the form desired for the production of the medicinal preparations. Therefore, the process that allows to transform rifaximin γ into rifaximin α or β in a valid industrial manner, or vice versa rifaximin β into rifaximin α, are important parts of the invention.

The process concerning the transformation of rifaximin γ into rifaximin α or rifaximin β comprises suspending rifaximin γ in a solvent mixture consisting of ethyl alcohol/water in 7:3 volumetric ratio, warming the suspension to a temperature between 38° C. and 50° C. and keeping it at this temperature under strong stifling for a time between 6 and 36 hours.

The suspension is then filtered, the solid is washed with water and dried; the polymorphic form β is obtained when drying is carried out to a water content between 5.0% and 6.0% measured by the Karl Fischer method, while the polymorphic form α is obtained when drying is continued to a water content between 2.0% and 3.0%.

The process for the preparation of the form γ starting from rifaximin α or β comprises dissolving the α or β form in ethyl alcohol under stifling, at a temperature between 50° C. and 60° C., adding demineralized water to an ethyl alcohol/water 7:3 volumetric ratio, cooling the solution to 30° C. under strong stifling, cooling the precipitate to 0° C. and keeping the suspension under stirring at 0° C. for a time between 6 and 24 hours. The suspension is then filtered, the solid is washed with water and dried to a water content lower than 2.0% thereby obtaining rifaximin γ.

The process for the transformation of the form α into the form β consists in keeping powder rifaximin α in an ambient having relative humidity higher than 50% for the time required to obtain a water content in the powder higher than 4.5%, which time is usually between 12 and 48 hours.

The process for the transformation of the form β into the form α consists in drying powder rifaximin β under vacuum or under conditions of normal pressure, optionally in the presence of a drying agent, at a temperature between the room temperature and 105° C., for a time between 2 and 72 hours, to obtain a water content in the powder lower than 4.5%, preferably between 2.0% and 3.0%.

It is evident from what stated above that during preservation of the product particular care should be taken so that the ambient conditions do not affect the water content of the product, by preserving the product in an environment having controlled humidity or in closed containers that allow no significant exchanges of water with the exterior.

Figure 2:
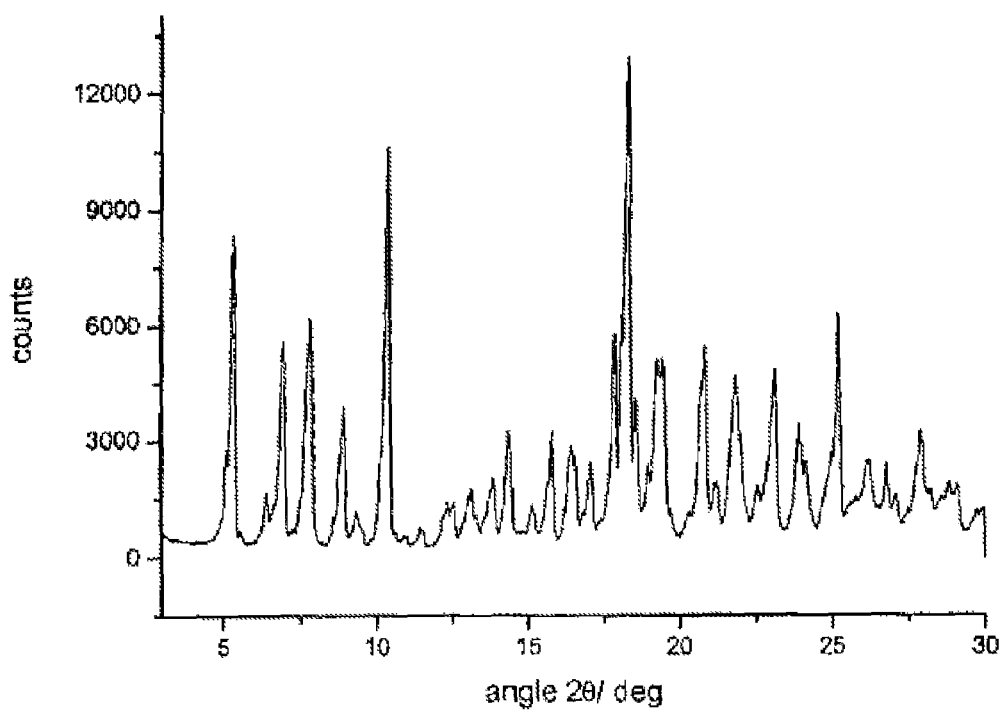
FIG. 2 is a powder X-ray diffractogram of rifaximin polymorphic form β.

The rifaximin α polymorph is characterized by a water content lower than 4.5%, preferably between 2.0% and 3.0% and by a powder X-ray diffractogram (reported in FIG. 1) which shows peaks at the values of the diffraction angles 2θ of 6.6°; 7.4°; 7.9°; 8.8°; 10.5°; 11.1°; 11.8°; 12.9°; 17.6°; 18.5°; 19.7°; 21.0°; 21.4°; 22.1°. The rifaximin β polymorph is characterized by a water content higher than 4.5%, preferably between 5.0% and 6.0%, and by a powder X-ray diffractogram (reported in FIG. 2) which shows peaks at the values of the diffraction angles 2θ of 5.4°; 6.4°; 7.0°; 7.8°; 9.0°; 10.4°; 13.1°; 14.4°; 17.1°; 17.9°; 18.3°; 20.9°.

Figure 3:
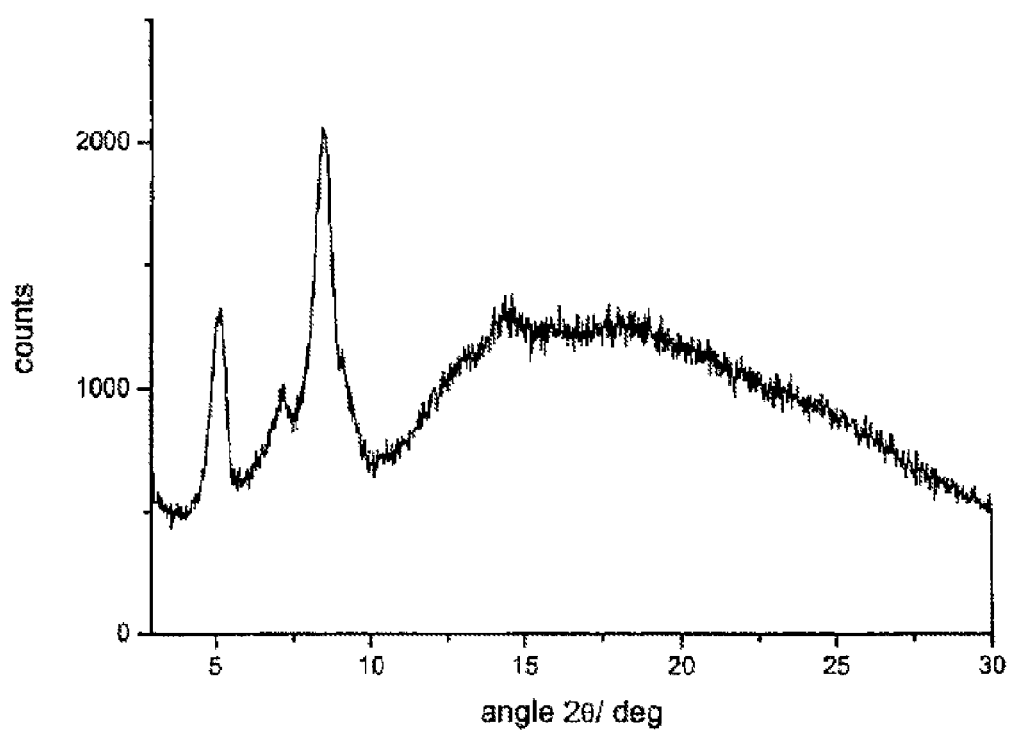
FIG. 3 is a powder X-ray diffractogram of rifaximin polymorphic form γ.

The rifaximin γ polymorph is characterized by a powder X-ray diffractogram much poorer because of the poor crystallinity; the significant peaks are at the values of the diffraction angles 2θ of 5.0°; 7.1°; 8.4° as reported in FIG. 3.

The diffractograms have been carried out using a Philips X'Pert instrument fitted with Bragg-Brentano geometry and under the following working conditions:
X-ray tube: Copper
Radiation used: K (α1), K (α2)
Tension and current of the generator: KV 40, mA 40
Monocromator: Graphite
Step size: 0.02
Time per step: 1.25 seconds
Starting and final angular 2θ value: 3.0°÷30.0°

The evaluation of the water content in the analyzed samples has always been carried out by means of the Karl Fischer method.

Rifaximin α, rifaximin β and rifaximin γ significantly differ from each other also in terms of bioavailability and intrinsic dissolution.

A bioavailability study of the three polymorphs has been carried out on Beagle female dogs, by feeding them orally with a dose of 100 mg/kg of one of the polymorphs, collecting blood samples from the jugular vein of each animal before each dosing and 1, 2, 4, 6, 8 and 24 hours after each dosing, transferring the samples into tubes containing heparin and separating the plasma by centrifugation.

The plasma has been assayed for rifaximin on the validated LC-MS/MS (Liquid Chromathography-Mass Spectrometry/Mass Spectrometry) method and the maximum plasma concentration observed ($C_{max}$), the time to reach the ($C_{max}$) ($t_{max}$), and the area under the concentration-time curve (AUC) have been calculated.

The experimental data reported in the following table 1 clearly show that rifaximin α and rifaximin β are negligibly absorbed, while rifaximin γ is absorbed at a value ($C_{max}$=0.668 µg/ml) comprised in the range of from 0.1 to 1.0 µg/ml.

TABLE 1

Pharmacokinetic parameters for rifaximin polymorphs following single oral administration of 100 mg/kg by capsules to female dogs.

|  | $C_{max}$ ng/ml Mean | $t_{max}$ h Mean | $AUC_{0-24}$ ng · h/ml Mean |
|---|---|---|---|
| Polimorph α | 2.632 | 9.5 | 13 |
| Polimorph β | 1.096 | 4 | 11 |
| Polimorph γ | 668.22 | 2.25 | 3908 |

Intrinsic dissolution tests have been carried out on each of the three polymorphs according to the method described in the monograph 1087 at pages 2512-2513 of the USP (U.S. Pharmacopoeia) 27, clearly showing significant differences among rifaximin α, rifaximin β and rifaximin γ.

A sample of each rifaximin polymorph has been put into a die and compressed at 5 tons by means of a punch of a hydraulic press to obtain a compacted pellet.

The die-holder containing the compacted pellet has then been mounted on a laboratory stirring device, immersed in a dissolution medium and rotated by means of the stirring device.

The test, carried out in a dissolution medium made of aqueous phosphate buffer at ph 7.4 and of sodium lauryl sulfate at a temperature of 37±0.5° C., has shown significant differences among the instrinsic dissolution rates exhibited by the three polymorphs.

Rifaximin α has shown disintegration of the compacted pellet within 10 minutes so that it has not been possible to calculate the value of its intrinsic dissolution, while the intrinsic dissolution of rifaximin γ has been about ten times as much that of rifaximin β in accordance with its bioavailability which is more than hundred times as much that of rifaximin β.

The above experimental results further point out the differences existing among the three rifaximin polymorphs.

The forms α, β and γ can be advantageously used in the production of medicinal preparations having antibiotic activity, containing rifaximin, for both oral and topical use. The medicinal preparations for oral use will contain rifaximin α or β or γ together with the usual excipients, for example diluting agents such as mannitol, lactose and sorbitol; binding agents such as starchs, gelatines, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starchs, celluloses, alginates, gums and reticulated polymers; coloring, flavoring and sweetening agents.

The present invention relates to all of the solid preparations administrable by the oral route, for instance coated and uncoated tablets, of soft and hard gelatine capsules, sugar-coated pills, lozenges, wafer sheets, pellets and powders in sealed packets.

The medicinal preparations for topical use will contain rifaximin α or β or γ together with usual excipients, such as white petrolatum, white wax, lanoline and derivatives thereof, stearylic alcohol, propylene glycol, sodium lauryl sulfate, ethers of fatty polyoxyethylene alcohols, esters of fatty polyoxyethylene acids, sorbitan monostearate, glyceryl monostearate, propylene glycol monostearate, polyethylene glycols, methylcellulose, hydroxy propylmethylcellulose, sodium carboxymethylcellulose, colloidal aluminium and magnesium silicate, sodium alginate.

The present invention relates to all of the topical preparations, for instance ointments, pomades, creams, gels and lotions.

The invention is further illustrated by some examples. Such examples are not to be taken as a limitation of the invention, it is in fact evident that the α, β and γ forms can be obtained by suitably combining between them the above mentioned conditions of crystallization and drying.

EXAMPLE 1

Preparation of Raw Rifaximin and of Dried Raw Rifaximin

In a three-necked flask equipped with mechanic stirrer, thermometer and reflux condenser, 120 ml of demineralized water, 96 ml of ethyl alcohol, 63.5 g of rifamycin 0 and 27.2 g of 2-amino-4-methylpyridine are loaded in succession at room temperature. After loading, the mass is heated at 47±3° C. and kept under stirring at this temperature for 5 hours, then is cooled to 20±3° C. and, during 30 minutes, is added with a mixture, prepared separately, of 9 ml of demineralized water, 12.6 ml of ethyl alcohol, 1.68 g of ascorbic acid and 9.28 g of aqueous concentrated hydrochloric acid. After completion of the addition, the mass is kept under stirring for 30 minutes at an inner temperature of 20±3° C. then 7.72 g of concentrated hydrochloric acid are dripped until a pH equal to 2.0, while keeping said temperature.

After completion of the addition, the mass is kept under stifling for 30 minutes, keeping an inner temperature of 20° C., then the precipitate is filtered and washed with a mixture of 32 ml of demineralized water and of 25 ml of ethyl alcohol. The resulting "raw rifaximin" (89.2 g) is dried under vacuum at room temperature for 12 hours obtaining 64.4 g of "dried raw rifaximin" which shows a water content of 5.6% and a diffractogram corresponding to the polymorphic form β. The product is further dried under vacuum until constant weight to afford 62.2 g of dried raw rifaximin having a water content of 2.2%, whose diffractogram corresponds to the polymorphic form α.

The product is hygroscopic and the obtained polymorphic form is reversible: the polymorphic form α absorbs water from atmospheric humidity, depending on the relative humidity and the exposure time. When the water content absorbed by the polymorphic form α becomes higher than 4.5%, polymorphous α turns to polymorphous β. This in its turn loses part of water by drying, changing into the polymorphic form α when a water content between 2.0% and 3.0% is reached.

EXAMPLE 2

Preparation of Rifaximin γ

163 ml of ethyl alcohol and 62.2 g of dried raw rifaximin are loaded at room temperature into a three-necked flask equipped with mechanic stirrer, thermometer and reflux condenser. The suspension is heated at 57±3° C. under stifling until complete dissolution of the solid, and added with 70 ml of demineralized water at this temperature in 30 minutes. After completion of the addition the temperature is brought to 30° C. in 40 minutes and kept at this value until complete crystallization, then the temperature is further lowered to 0° C. in 2 hours and kept at this value for 6 hours. The suspension is then filtered and the solid is washed with 180 g of demineralized water and dried under vacuum at room temperature until constant weight, thereby obtaining 52.7 g of pure rifaximin γ having water content of 1.5%.

The form γ is characterized by a powder X-ray diffractogram showing significant peaks at diffraction angles 2θ of 5.0°; 7.1°; 8.4°.

EXAMPLE 3

Preparation of Rifaximin α

62.2 Grams of dried raw rifaximin and 163 ml of ethyl alcohol are loaded at room temperature into a three-necked flask equipped with mechanic stirrer, thermometer and reflux condenser. The suspension is heated at 57±3° C. until complete dissolution of the solid and then 70 ml of demineralized water are added at this temperature during 30 minutes. After completion of the addition, the temperature is brought to 30° C. during 40 minutes and is kept at this value until plentiful crystallization. The temperature of the suspension is then brought to about 40° C. and kept at this value during 20 hours under stifling; then the temperature is decreased to 0° C. in 30 minutes and the suspension is immediately filtered. The solid is washed with 180 ml of demineralized water and dried under vacuum at room temperature until constant weight, thereby obtaining 51.9 g of rifaximin form α are obtained with a water content equal to 2.5% and a powder X-ray diffractogram showing peaks at values of angles 2θ of 6.6°; 7.4°; 7.9°; 8.8°; 10.5°; 11.1°; 11.8°; 12.9°; 17.6°; 18.5°; 19.7°; 21.0°; 21.4°; 22.1°.

EXAMPLE 4

Preparation of Rifaximin α

89.2 Grams of raw rifaximin and 170 ml of ethyl alcohol are loaded at room temperature into a three-necked flask equipped with mechanic stirrer, thermometer and reflux condenser, then the suspension is heated at 57±3° C. until complete dissolution of the solid. The temperature is brought to 50° C. and then 51.7 ml of demineralized water are added at this temperature during 30 minutes. After completion of the addition the temperature is brought to 30° C. in one hour and the suspension is kept for 30 minutes at this temperature obtaining a plentiful crystallization. The temperature of the suspension is brought to 40° C. and kept at this value during 20 hours under stirring and then further lowered to 0° C. during 30 minutes after which the suspension is immediately filtered. The solid is washed with 240 ml of demineralized water and dried under vacuum at 65° C. until constant weight thereby obtaining 46.7 g of rifaximin α with a water content equal to 2.5%.

EXAMPLE 5

Preparation of Rifaximin α

Example 3 is repeated, but increasing to 50° C. the temperature at which the suspension is kept and lowering to 7 hours the time in which the suspension is kept at this temperature. The product obtained is equal to that of example 3.

EXAMPLE 6

Preparation of Rifaximin β

The crystallization of the dried raw rifaximin is carried out according to the process described in example 3. Drying under vacuum at room temperature is monitored by Karl Fischer and stopped when the water content reaches 5.0%: 52.6 g of rifaximin β are obtained characterized by a powder X-ray diffractogram showing peaks at values of angles 2θ of 5.4°; 6.4°; 7.0°; 7.8°; 9.0°; 10.4°; 13.1°, 14.4°; 17.1°; 17.9°; 18.3°; 20.9°.

EXAMPLE 7

Preparation of Rifaximin α Starting from Rifaximin γ

Grams of rifaximin γ are suspended in a mixture of 13 ml of ethyl alcohol and 5.6 ml of water and the suspension is heated at 40° C. during 24 hours under stirring in a 50 ml flask equipped with condenser, thermometer and mechanic stirrer. The suspension is then filtered and the solid is washed with water, then dried under vacuum at room temperature until constant weight. 4 Grams of rifaximin are obtained showing a powder X-ray diffractogram corresponding to that of the polymorphic form α and a water content equal to 2.6%.

EXAMPLE 8

Preparation of Rifaximin γ Starting from Rifaximin α

15 Grams of rifaximin form α and 52.4 ml of ethyl alcohol are loaded into a 250 ml three-necked flask equipped with reflux condenser, thermometer and mechanical stirrer; the suspension is heated under stirring at the temperature of 50° C. until complete dissolution of the solid.

The clear solution is added with 22.5 ml of water in 30 minutes under stirring, cooled to 30° C. and kept at this temperature for 30 minutes. The formed suspension is cooled to 0° C. under strong stirring and kept at this temperature during 6 hours. After this time, part of the suspension is taken, filtered, washed with demineralized water and dried under vacuum at 30° C. until constant weight.

The resulting product, 3.7 g, shows a diffractogram consistent with that of the form γ and a water content of 1.7%.

The remaining part of the suspension is kept at 0° C. for further 18 hours under strong stirring and then is filtered, washed with demineralized water and dried at 30° C. under vacuum until constant weight. 9 Grams of product showing a diffractogram consistent with that of the form γ and a water content equal to 1.6% are obtained.

EXAMPLE 9

Preparation of Rifaximin α Starting from Rifaximin β

5 Grams of rifaximin β having a water content equal to 5.0% are dried under vacuum at +30° C. during 8 hours obtaining 4.85 g of rifaximin α having a water content equal to 2.3%.

EXAMPLE 10

Preparation of Rifaximin β Starting from Rifaximin α

5 Grams of rifaximin α having a water content equal to 2.5% are kept during 40 hours in an atmosphere containing a relative humidity equal to 56% made by means of a saturated aqueous solution of calcium nitrate tetrahydrate. 5.17 Grams of rifaximin β with a water content equal to 5.9% are obtained after this time.

EXAMPLE 11

Bioavailability in Dogs by Oral Route

Twelve 20 week pure-bred Beagle females dogs, and weighing between 5.0 and 7.5 kg, have been divided into three groups of four.

The first of these three groups has been treated with rifaximin α, the second with rifaximin β and third with rifaximin γ according to the following procedure.

Each dog received orally 100 mg/kg of one of the rifaximin polymorphs in gelatin capsules and 2 ml blood samples were collected from the jugular vein of each animal before each administration and 1, 2, 4, 6, 8 and 24 hours after the administration. Each sample was transferred into an heparinized tube and was centrifuged; the plasma was divided into 500 two aliquots and frozen at −20° C.

The rifaximin contained in the plasma was assayed by means of the validated LC-MS/MS method and the following parameters were calculated according to standard non-compartmental analysis:

$C_{max}$=maximum plasma concentration of rifaximin observed in the plasma;

$T_{max}$=time at which the $C_{max}$ is reached;

AUC=area under the concentration-time curve calculated through the linear trapezoidal rule.

The results reported in the following table 2 clearly show how the rifaximin γ is very much more absorbed, more than 102 times, in respect of rifaximin α and rifaximin β which are practically not absorbed.

TABLE 2

Pharmacokinetic parameters for rifaximin polymorphs following single oral administration of 100 mg/kg by capsules to female dogs.

| | $C_{max}$ ng/ml Mean | $t_{max}$ h Mean | $AUC_{0-24}$ ng · h/ml Mean |
|---|---|---|---|
| rifaximin α | 2.632 | 9.5 | 13 |
| rifaximin β | 1.096 | 4 | 11 |
| rifaximin γ | 668.22 | 2.25 | 3908 |

EXAMPLE 12

Intrinsic Dissolution Test

A sample of 100 mg of each rifaximin polymorph was submitted to the intrinsic dissolution test carried out as described in the monograph 1087 at pages 2512-2513 of the USP (U.S. Pharmacopoeia) 27.

100 Milligrams of a rifaximin polymorph were put into a die and compressed for 1 minute under a pressure of 5 tons by means of a punch in a hydraulic press.

A compacted pellet was formed in the die with a single face of defined area exposed on the bottom of the die so that from 50% to 75% of the compacted pellet could dissolve in an appropriate dissolution medium.

The holder containing the die was mounted on a laboratory stifling device, immersed in a glass vessel containing a dissolution medium and rotated at a rotation speed of 100 rpm by means of the stifling device, while keeping the temperature of the dissolution medium at 37±0.5° C. The dissolution medium contained in the glass vessel consisted of 1000 ml of 0.1 M aqueous phosphate buffer pH 7.4 containing 4.5 g of sodium lauryl sulfate and was kept at 37±0.5° C. for the whole duration of the test.

Samples of 2 ml of solution were taken after 15, 30, 45 and 60 minutes from the start of the dissolution procedure and analyzed by HPLC for the amount of rifaximin dissolved.

The sample containing rifaximin α systematically showed disintegration of the compacted pellet within 10 minutes and said phenomenon was also present at lower concentrations (0.1% and 0.3%) of sodium lauryl sulfate and even in absence of said surfactant, so that the value of its intrinsic dissolution could not be calculated.

The intrinsic dissolution of rifaximin γ was about ten times as much that of rifaximin β at every time, as it can be inferred by the experimental results shown in the following table 3.

TABLE 3

Intrinsic dissolution in 0.1M aqueous phosphate buffer pH 7.4 with 0.45% sodium lauryl sulfate

| | Rifaximin dissolved (mg/cm$^2$) | |
|---|---|---|
| Time (min) | β polymorph | γ polymorph |
| 15 | 0.28 | 2.46 |
| 30 | 0.50 | 4.52 |
| 45 | 0.72 | 6.44 |
| 60 | 0.94 | 9.04 |
| Intrinsic dissolution rate (mg/min/cm$^2$) | 0.0147 | 0.1444 |

What is claimed is:

1. A pharmaceutical composition comprising a polymorphic form of rifaximin together with a pharmaceutically acceptable carrier, wherein the polymorphic form is form α, having x-ray powder diffraction pattern peaks at about:
   7.4°, 7.9°, and 11.8°; or
   7.4°, 8.8°, and 11.8°; or
   7.4°, 10.5°, and 11.8°; or
   7.4°, 11.1°, and 11.8°; or
   7.4°, 11.8° and 12.9°; or
   7.4°, 11.8° and 17.6°; or
   7.4°, 11.8° and 19.7°; or
   7.4°, 11.8° and 21.4°; or
   7.4°, 11.8° and 22.1°, or
   7.4°,11.1°, and 12.9°; or
   7.4°, 11.1°, and 19.7°; or
   7.4°, 12.9°, and 19.7°; or
   11.1°, 11.8°, and 19.7°; or
   11.1°, 19.7°, and 21.4°; or
   11.1°, 19.7°, and 22.1°, or
   11.8°, 12.9°, and 19.7°; or
   11.8°, 19.9°, and 22.1°, 2θ.

2. The pharmaceutical composition of claim 1, wherein after administration of the pharmaceutical composition to a patient, an observed plasma concentration of rifaximin in the patient is negligible.

3. The pharmaceutical composition of claim 1, wherein the composition further comprises an excipient.

4. The pharmaceutical composition of claim 2, wherein the excipient is selected from the group consisting of a diluting agent, a binding agent, a lubricating agent, a disintegrating agent, a coloring agent, a flavoring agent, and a sweetening agent.

5. The pharmaceutical composition of claim 2, wherein the composition is for oral use and is in a form selected from the group consisting of coated or uncoated tablets, hard or soft gelatin capsules, sugar-coated pills, lozenges, wafer sheets, pellets, and powders in sealed packet.

6. The pharmaceutical composition of claim 2, wherein the composition comprises one or more of colloidal silicon dioxide, hydroxypropyl methylcellulose, cellulose, microcrystalline cellulose, propylene glycol, sodium starch glycolate.

7. A pharmaceutical composition comprising a polymorphic form of rifaximin together with a pharmaceutically acceptable carrier, wherein the polymorphic form is form β, having x-ray powder diffraction pattern peaks at about:
   5.4°, 6.4°, and 7.0°, or
   5.4°, 6.4°, and 7.8°; or
   5.4°, 6.4°, and 9.0°; or
   5.4°, 6.4°, and 10.4°; or
   5.4°, 6.4°, and 13.1°, or
   5.4° and 7.0°, and 14.4°; or
   5.4°, 10.4°, and 18.3°; or
   5.4°, 10.4°, and 20.9°; or
   5.4°, 10.4°, and 17.1°, or
   6.4°, 7.0°, and 10.4°; or
   6.4°, 7.8° and 10.4°; or
   6.4°, 9.0° and 10.4°; or
   6.4°, 10.4°, and 14.4°; or
   10.4°, 13.1°, and 14.4°; or
   10.4°, 17.1°, and 17.9°; or
   10.4°, 17.9°, and 18.3°; or
   10.4°, 17.9°, and 20.9°; or
   10.4°, 18.3°, and 20.9°; or
   14.4°, 17.1°, and 18.3°; or
   17.1°, 18.3°, and 20.9°; or
   14.4°, 17.1°, and 20.9°, 2θ.

8. The pharmaceutical composition of claim 7, wherein after administration of the pharmaceutical composition to a patient, an observed plasma concentration of rifaximin in the patient is negligible.

9. The pharmaceutical composition of claim 7, further comprising an excipient.

10. The pharmaceutical composition of claim 9, wherein the excipient is selected from the group consisting of a diluting agent, a binding agent, a lubricating agent, a disintegrating agent, a coloring agent, a flavoring agent, and a sweetening agent.

11. The pharmaceutical composition of claim 7, wherein the composition is for oral use and is in a form selected from the group consisting of coated or uncoated tablets, hard or soft gelatin capsules, sugar-coated pills, lozenges, wafer sheets, pellets, and powders in sealed packet.

12. The pharmaceutical composition of claim 10, wherein the composition comprises one or more of colloidal silicon dioxide, hydroxypropyl methylcellulose, cellulose, microcrystalline cellulose, propylene glycol, sodium starch glycolate.

13. A pharmaceutical composition comprising a polymorphic form of rifaximin together with a pharmaceutically acceptable carrier, wherein the polymorphic form is form γ, having x-ray powder diffraction pattern peaks at about 5.0°, 7.1°, and 8.4° 2θ and an intrinsic dissolution rate of about 0.14 mg/min/cm$^2$.

14. The pharmaceutical composition of claim 13, wherein after administration of the pharmaceutical composition to a patient, an observed plasma concentration of rifaximin is of about 670 ng/ml.

15. The pharmaceutical composition of claim 14, wherein the composition further comprises an excipient.

16. The pharmaceutical composition of claim 15, wherein the excipient is selected from the group consisting of a diluting agent, a binding agent, a lubricating agent, a disintegrating agent, a coloring agent, a flavoring agent, and a sweetening agent.

17. The pharmaceutical composition of claim 14, wherein the composition is for oral use and is in a form selected from the group consisting of coated or uncoated tablets, hard or soft gelatin capsules, sugar-coated pills, lozenges, wafer sheets, pellets, and powders in sealed packet.

18. The pharmaceutical composition of claim 16, wherein the composition comprises one or more of colloidal silicon dioxide, hydroxypropyl methylcellulose, cellulose, microcrystalline cellulose, propylene glycol, sodium starch glycolate.

* * * * *

UNITED STATES PATENT AND TRADEMARK OFFICE
CERTIFICATE OF CORRECTION

PATENT NO. : 8,853,231 B2
APPLICATION NO. : 13/679602
DATED : October 7, 2014
INVENTOR(S) : Viscomi et al.

It is certified that error appears in the above-identified patent and that said Letters Patent is hereby corrected as shown below:

Title Page, Item (72) Inventor is corrected to read:
-- Giuseppe Claudio Viscomi, Bologna (IT);
Manuela Campana, Bologna (IT);
Dario Braga, Bologna (IT);
Donatella Confortini, Bologna (IT);
Vincenzo Cannata, Bologna (IT);
Paolo Righi, Bologna (IT);
Goffredo Rosini, Bologna (IT);
Denis Severini, Santarcangelo di Romagna (IT) --.

Signed and Sealed this
Eighteenth Day of August, 2015

Michelle K. Lee
*Director of the United States Patent and Trademark Office*